(12) United States Patent
Luyten et al.

(10) Patent No.: US 6,413,755 B1
(45) Date of Patent: Jul. 2, 2002

(54) HUMAN CHECKPOINT KINASE, HCDS1, COMPOSITIONS AND METHODS

(75) Inventors: Walter H. M. L. Luyten, Beerse (BE); Andrew E. Parker, Cheshire (GB); Clare McGowan, Del Mar; Alessandra Blasina, San Diego, both of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/529,093

(22) PCT Filed: Oct. 21, 1998

(86) PCT No.: PCT/EP98/06981

§ 371 (c)(1), (2), (4) Date: Apr. 7, 2000

(87) PCT Pub. No.: WO99/25843

PCT Pub. Date: May 27, 1999

(30) Foreign Application Priority Data

Oct. 22, 1997 (GB) .............................................. 9722320

(51) Int. Cl.[7] .............................. C12N 9/12; C12N 9/00; C07K 16/00; C07K 1/00; C07K 14/00
(52) U.S. Cl. ...................... 435/194; 435/183; 435/69.1; 530/387.1; 530/350; 536/23.1
(58) Field of Search .................. 435/6, 69.1, 320.1, 435/252.1, 91.2, 183, 194; 536/23.1, 24.3; 530/350, 387.1

(56) References Cited

U.S. PATENT DOCUMENTS 6,218,109 B1 * 4/2001 Elledge et al.

OTHER PUBLICATIONS

Peng, C–Y et al., 1997, "Mitotic and G2 Checkpoint Control: Regulation of 14–3–3 Protein Binding by Phosphorylation of Cdc25C on Serine–216" Science 277:1501–1505.

Hartwell and Kastan, 1994, "Cell Cycle Control and Cancer" Science 266: 1821–1828.

Elledge, 1996, "Cell Cycle Checkpoints: Preventing an Identity Crisis" Science 274:1664–1672.

Sanchez et al., 1997, "Conservation of the Chk1 Checkpoint Pathway in Mammals: Linkage of DNA Damage to Cdk Regulation through Cdc25" Science 277:1497–1501.

Lindsay et al., 1998, "S–phase–specific activation of Cds1 kinase defines a subpathway of the checkpoint response in Schizosaccharomyces pombe" Genes & Development 12:382–395.

Boddy et al., 1998, "Replication Checkpoint Enforeced by Kinases Cds1 and Chk1" Science 280:909–912.

Allen et al., 1994, "The SAD1/RAD53 protein kinase controls multiple checkpoints and DNA damage–induced transcription in yeast" Genes & Development 8:2416–2428.

Murakami & Okayama, 1995, "A kinase from fission yeast responsible for blocking mitosis in S phase" Nature 374:817–819.

Stern et al., 1990, "Spk1, a New Kinase from Saccharomyces cerevisiae, Phosphorylates Protein on Serine, Threonine, and Tyrosine" Molecular and Cellular Biology 11(2):987–1001.

Baker et al., 1994, "Complete Transposition requires four active monomers in the Mu transposase tetramer" Genes & Development 8:2416–2428.

Murakami et al. A kinase from fission yeast responsible for blocking mitosis in phase Nature vol. 374 Apr. 27, 1995.*

* cited by examiner

Primary Examiner—Remy Yucel
Assistant Examiner—Konstantua Katcheves
(74) Attorney, Agent, or Firm—Olson & Hierl, Ltd.

(57) ABSTRACT

The invention provides for a novel human checkpoint kinase gene, hCDS 1, translated protein, compositions, methods, and kits.

1 Claim, 3 Drawing Sheets

FIG. 1

HCDS1 cDNA nucleotide sequence

```
   1   actagtgatt actcacaggg ctcgagcggc cgcccgggca ggtcaggtgg    50
  51   gctcacgcgg tcgtgatgtc tcgggagtcg gatgttgagg ctcagcagtc   100
 101   tcatggcagc agtgcctgtt cacagcccca tggcagcgtt acccagtccc   150
 151   aaggctcctc ctcacagtcc cagggcatat ccagctcctc taccagcacg   200
 201   atgccaaact ccagccagtc ctctcactcc agctctggga cactgagctc   250
 251   cttagagaca gtgtccactc aggaactcta ttctattcct gaggaccaag   300
 301   aacctgagga ccaagaacct gaggagccta ccctgcccc ctgggctcga    350
 351   ttatgggccc ttcaggatgg atttgccaat cttgaatgtg tgaatgacaa   400
 401   ctactggttt gggagggaca aaagctgtga atattgcttt gatgaaccac   450
 451   tgctgaaaag aacagataaa taccgaacat acagcaagaa cactttcgg    500
 501   attttcaggg aagtgggtcc taaaaactct tacattgcat acatagaaga   550
 551   tcacagtggc aatggaacct tgtaaatac agagcttgta gggaaggaa     600
 601   aacgccgtcc tttgaataac aattctgaaa ttgcactgtc actaagcaga   650
 651   aataaagttt ttgtctttt tgatctgact gtagatgatc agtcagttta    700
 701   tcctaaggca ttaagagatg aatacatcat gtcaaaaact cttggaagtg   750
 751   gtgcctgtgg agaggtaaag ctggctttcg agaggaaaac atgtaagaaa   800
 801   gtagccataa agatcatcag caaaaggaag tttgctattg gttcagcaag   850
 851   agaggcagac ccagctctca atgttgaaac agaaatagaa attttgaaaa   900
 901   agctaaatca tccttgcatc atcaagatta aaacttttt tgatgcagaa    950
 951   gattattata ttgttttgga attgatggaa ggggagagc tgtttgacaa    1000
1001   agtggtgggg aataaacgcc tgaaagaagc tacctgcaag ctctatttt    1050
1051   accagatgct cttggctgtg cagtaccttc atgaaaacgg tattatacac   1100
1101   cgtgacttaa agccagagaa tgttttactg tcatctcaag aagaggactg   1150
1151   tcttataaag attactgatt ttgggcactc caagattttg ggagagacct   1200
1201   ctctcatgag aaccttatgt ggaaccccca cctacttggc gcctgaagtt   1250
1251   cttgtttctg ttgggactgc tgggtataac cgtgctgtgg actgctggag   1300
1301   tttaggagtt attcttttta tctgccttag tgggtatcca cctttctctg   1350
1351   agcataggac tcaagtgtca ctgaaggatc agatcaccag tggaaaatac   1400
1401   aacttcattc ctgaagtctg gcagaagtc tcagagaaag ctctggacct    1450
1451   tgtcaagaag ttgttggtag tggatccaaa ggcacgtttt acgacagaag   1500
1501   aagccttaag acaccgtgg cttcaggatg aagacatgaa gagaaagttt    1550
1551   caagatcttc tgtctgagga aaatgaatcc acagctctac cccaggttct   1600
1601   agcccagcct tctactagtc gaaagcggcc ccgtgaaggg gaagccgagg   1650
1651   gtgccgagac cacaaagcgc ccagctgtgt gctgctgt gttgtgaact     1700
1701   ccgtggtttg aacacgaaag aaatgtacct tctttcactc tgtcatcttt   1750
1751   cttttctttg agtctgtttt tttatagttt gtatttaat tatgggaata    1800
1801   attgcttttt cacagtcact gatgtacaat taaaacctg atggaacctg    1850
1851   gaaaaaaa
```

FIG. 2

Predicted hCDS1 Amino acid sequence

```
1    MSRESDVEAQ QSHGSSACSQ PHGSVTQSQG SSSQSQGISS  40
41   SSTSTMPNSS QSSHSSSGTL SSLETVSTQE LYSIPEDQEP  80
81   EDQEPEEPTP APWARLWALQ DGFANLECVN DNYWFGRDKS 120
121  CEYCFDEPLL KRTDKYRTYS KKHFRIFREV GPKNSYIAYI 160
161  EDHSGNGTFV NTELVGKGKR RPLNNNSEIA LSLSRNKVFV 200
201  FFDLTVDDQS VYPKALRDEY IMSKTLGSGA CGEVKLAFER 240
241  KTCKKVAIKI ISKRKFAIGS AREADPALNV ETEIEILKKL 280
281  NHPCIIKIKN FFDAEDYYIV LELMEGGELF DKVVGNKRLK 320
321  EATCKLYFYQ MLLAVQYLHE NGIIHRDLKP ENVLLSSQEE 360
361  DCLIKITDFG HSKILGETSL MRTLCGTPTY LAPEVLVSVG 400
401  TAGYNRAVDC WSLGVILFIC LSGYPPFSEH RTQVSLKDQI 440
441  TSGKYNFIPE VWAEVSEKAL DLVKKLLVVD PKARFTTEEA 480
481  LRHPWLQDED MKRKFQDLLS EENESTALPQ VLAQPSTSRK 520
521  RPREGEAEGA ETTKRPAVCA AVL
```

```
HCDS1    :  MPNSSQSSHSSSGTLSSLETVSTQELYSIPEDQEPEDQEPEEPTPAPWARLWALQDGFANLECVNDNYW-FGRDKSCEY   :  78
S.p.CDS1 :  ME----EPEEATQALQEAPLHVSQNIAKQVNN------ENVFMKLVMTRMLDGKTEVIPLTTDVHNGFWGFGRHKSCEV   :  70

HCDS1    :  CFDEPLLKRTDKYRTYSKKHFRIFREVGPKNSYIAYTEDHSGNGTFVNIELVGKKRPLNNSETALSLSRNK--------   :  152
S.p.CDS1 :  VLNGP--RVSNFHFEIYQGHRNDSDES--EN--VVFLHDHSSNGTFLNFERLAKNSRTILSNGDEIRIGLGVPKDEISF   :  143

HCDS1    :  -VFVFFDLTVDDQSVYPKALRDEYIMSKTLGSGACGEVKLAFERKTCNKVAIKIISKRKFAIGSAREADPALNVETEIE   :  230
S.p.CDS1 :  LCQVPVKHSRDSQKNMIKSENSHYEIIRTLGSGTFAVVKLAVEVNSGKWYAIKIINKRNILTSS-EKRATEMFQREID   :  221

HCDS1    :  ILKKINHPCIIKIKNFFDAED-YYIVLELMEGGELFDKVVGNKRIKEATCKLYFYQMLLAVQYLHENGIIHRDLKPENV   :  308
S.p.CDS1 :  ILKSLHHPGVVQCHEICENDDELFIVMEYVEGGDLMDFLIANGSIDEQDCKPLLKQLIETLLHLHKQGVTHRDIKPENI   :  300

HCDS1    :  LLSSQEEDCLIKITDFGHSKILGET-SLMRTLCGTPTYLAPEVLVSVGT---AGYNRAVDCMSLGVILFICLSGYPPFS   :  383
S.p.CDS1 :  LITN---DFHLKISDFGLAKVIHGTGTFLFIFCGTMGYLAPEVLRSKNVNLDGGYDDKVDIVSLGCVLYVMLTASIPFA   :  376

HCDS1    :  EHRTQVSLKDQITSGKYNFIPEVMAEVSEKALDIVKKLLVVDPKARFTTEEALRHPWLQDEDMKRKFQDLLSEENESTA   :  462
S.p.CDS1 :  SS--SQAKCIELISKGAYPIEPLLENEISBEGIDLINRMLEINPEKRISESEALQHPFYT------------------   :  435

HCDS1    :  LPQVLAQPSTSRKRPREGEAEGAETTKRPAVCAAVL   :  498
S.p.CDS1 :  ------VSTHEHRTPPSSSEHEATEQLNSSS-----   :  460
```

FIG. 3

HUMAN CHECKPOINT KINASE, HCDS1, COMPOSITIONS AND METHODS

BACKGROUND OF THE INVENTION

The integrity of the genome is of prime importance to a dividing cell. In response to DNA damage, eukaryotic cells rely upon a complex system of checkpoint controls to delay cell-cycle progression. The normal eukaryotic cell-cycle is divided into 4 phases (sequentially G1, S, G2, M) which correlate with distinct cell morphology and biochemical activity, and cells withdrawn from the cell-cycle are said to be in G0, or non-cycling state. When cells within the cell-cycle are actively replicating, duplication of DNA occurs in the S phase, and active division of the cell occurs in M phase. See generally Benjamin Lewin, *GENES VI* (Oxford University Press, Oxford, GB, Chapter 36, 1997). DNA is organized in the eukaryotic cell into successively higher levels of organization that result in the formation of chromosomes. Non-sex chromosomes are normally present in pairs, and during cell division, the DNA of each chromosome replicates resulting in paired chromatids. (See generally Benjamin Lewin, *GENES VI* (Oxford University Press, Oxford, GB, Chapter 5, 1997).

Checkpoint delays provide time for repair of damaged DNA prior to its replication in S-phase and prior to segregation of chromatids in M-phase (Hartwell and Weinert, 1989, *Science*, 246: 629–634). In many cases the DNA-damage response pathways cause arrest by inhibiting the activity of the cyclin-dependent kinases (Elledge, 1997, *Science*, 274: 1664–1671). In human cells the DNA-damage induced G2 delay is largely dependent on inhibitory phosphorylation of Cdc2 (Blasina et at., 1997, *Mol. Cell Biol.*, 8: 1–11; Jin et al., 1996, *J. Cell Biol.*, 134: 963–970), and is therefore likely to result from a change in the activity of the opposing kinases and phosphatases that act on Cdc2. However, evidence that the activity of these enzymes is substantially altered in response to DNA damage is lacking (Poon et al., 1997, *Cancer Res.*, 57: 5168–5178).

Three distinct Cdc25 proteins are expressed in human cells. Cdc25A is specifically required for the G1-S transition (Hoffmann et al., 1994, *EMBO J.*, 13: 4302–4310; Jinno et al., 1994, *EMBO J.*, 13: 1549–1556), whereas Cdc25B and Cdc25C are required for the G2-M transition (Gabrielli et al., 1996, *J. Cell Sci.*, 7: 1081–1093; Galaktionov et al., 1991, *Cell*, 67: 1181–1194; Millar et al., 1991, *Proc. Natl. Acad. Sci. USA*, 88: 10500–10504; Nishijima et al., 1997, *J. Cell Biol.*, 138: 1105–1116). The exact contribution of Cdc25B and Cdc25C to M-phase progression is not known.

Much of our current knowledge about checkpoint control has been obtained from studies using budding (*Saccharomyces cerevisiae*) and fission (*Schizosaccharomyces pombe*) yeast. A number of reviews of our current understanding of cell cycle checkpoints in yeast and higher eukaryotes have recently been published (Hartwell & Kastan, 1994, *Science*, 266: 1821–1828; Murray, 1994, *Current Biology*, 6: 872–876; Elledge, 1996, *Science*, 274: 1664–1672; Kaufmann & Paules, 1996, *FASEB J.*, 10: 238–247). In the fission yeast six gene products, rad1$^+$, rad3$^+$, rad9$^+$, rad17$^+$, rad26$^+$, and hus1$^+$ have been identified as components of both the DNA-damage dependent and DNA-replication dependent checkpoint pathways. In addition cds1$_+$ has been identified as being required for the DNA-replication dependent checkpoint and rad27$^+$/chk1$^+$ has been identified as required for the DNA-damage dependent checkpoint in yeast.

Several of these genes have structural homologues in the budding yeast and further conservation across eukaryotes has recently been suggested with the cloning of two human homologues of *S. pombe* rad3$^+$: ATM (ataxia telangiectasia mutated) (Savitsky et al., 1995, *Science*, 268: 1749–1753) and ATR (ataxia telangiectasia and rad3$^+$ related)(Bentley et al, 1996, *EMBO J.*, 15: 6641–6651; Cimprich et al., 1996, *Proc. Natl. Acad. Sci. USA*, 93: 2850–2855) and of a human homologue of *S. pombe* rad9$^+$ (Lieberman et al., 1996, *Proc. Natl. Acad. Sci. USA*, 93: 13890–13885).

While much is known about yeast checkpoint proteins and genes, this knowledge is not fully predictive of the existence of corresponding human genes or proteins, or their effector role in human cell-cycle control and regulation.

In order to develop new and more effective treatments and therapeutics for the amelioration of the effects of cancer, it is important to identify and characterize human checkpoint proteins and to identify mediators of their activity.

SUMMARY OF THE INVENTION

The present invention is directed to the discovery of a novel human checkpoint kinase gene hCDS1, protein and constructs and methods for the production and use of HCDS1.

In particular, the present invention encompasses a nucleic acid sequence which encodes for hCDS1, consisting of the nucleic acid sequence of SEQ ID NO.: 1. In particular, the invention encompasses the nucleic acid sequence from position 66 to 1694 of the nucleic acid sequence of SEQ ID NO.: 1, which translates into the hCDS1 protein. The present invention also encompasses nucleic acid constructs, vectors, plasmids, cosmids and the like which contain the nucleic acid sequence of SEQ ID NO.: 1. In particular, the present invention provides for nucleic acid vector constructs which contain the nucleic acid sequence of SEQ ID NO.: 1 and are capable of expressing protein from this nucleic acid sequence. The present invention encompasses nucleic acid vectors that are suitable for the transformation of host cells, whether eukaryotic or prokaryotic, suitable for incorporation into viral vectors, or suitable for in vitro protein expression. The present invention further embodies the nucleic acid sequence of SEQ ID NO.: 1 in tandem with, or otherwise in conjunction with additional nucleic acids for the generation of fusion protein products containing at least the functional segment of the protein encoded for by the nucleic acid of SEQ ID NO.: 1. The present invention also encompasses the nucleic acid of SEQ ID NO.: 1 adapted for use as a naked DNA transformant for incorporation and expression in target cells. The present invention also provides for anti-sense DNA molecule formulations which are the complement to the nucleic acid sequence of SEQ ID NO.: 1, and fragments thereof, whether complementary to contiguous or discontinuous portions of the nucleic acid sequence of SEQ ID NO.: 1. The present invention also provides for compositions incorporating modified nucleotides or backbone components which encode for the nucleic acid sequence of SEQ ID NO.: 1, its complement, or fragments thereof. Such modified nucleotides and nucleic acids are known in the art (see for example Verma et al., *Ann. Rev. Biochem.* 67: 99–134 (1998)). Thus the present invention encompasses modified nucleic acids which incorporate, for example, intemucleotide linkage modification, base modifications, sugar modification, nonradioactive labels, nucleic acid cross-linking, and altered backbones including PNAs (polypeptide nucleic acids).

The present invention provides for the novel human checkpoint kinase protein hCDS1, which consists of the amino acid sequence of SEQ ID NO.: 2. The invention encompasses hCDS1 protein produced by recombinant DNA technology and expressed in vivo or in vitro. The invention thus encompasses hCDS1 protein produced by transformed host cells in small-scale or large-scale production. The invention encompasses complete hCDS1 protein, in either glycosylated or unglycosylated forms, produced by either eukaryotic or prokaryotic cells. The present invention provides for hCDS1 protein expressed from mammalian, insect, plant, bacterial, fungal, or any other suitable host cell. The present invention encompasses hCDS1 protein that is produced as a fusion protein product, conjugated to a solid support, or hDCS1 protein which is labeled with any chemical, radioactive, fluorescent, chemiluminescent or otherwise detectable marker. The present invention also provides for hDCS1 protein isolated from natural sources and enriched in purity over that found in nature. The present invention also provides for pharmaceutical formulations of hDCS1 protein and formulations of the hCDS1 protein in pharmaceutically acceptable carriers or excipients.

The present invention encompasses any nucleic acid sequence which would encode for the amino acid sequence of SEQ ID NO.: 2, and the embodiments of these nucleic acid sequences as described for SEQ ID NO.: 1, as the nucleic acid code for generating any nucleic acid sequence which will encode for a protein having the amino acid sequence of SEQ ID NO.: 2 is predictable to one of skill in the art.

The present invention encompasses antibodies which bind specifically to the hDCS1 protein, either polyclonal or monoclonal, as generated by the immunization of a mammal with protein having the amino acid sequence of SEQ ID NO.: 2, or fragments thereof.

The present invention also encompasses equivalent proteins where substitutions of amino acids in the sequence of SEQ ID NO.: 2 that are reasonably predictable as being equivalent, and the embodiments thereof as described for SEQ ID NO.: 2. For example, non-polar (hydrophobic side-chain) amino acids alanine, valine, leucine, isoleucine, proline, phenylalanine, tryptophan, methionine; uncharged polar amino acids glycine, serine, threonine, cysteine, tyrosine, asparagine, glutamine; charged polar amino acids aspartic acid, glutamic acid; basic amino acids lysine, arginine, and histidine are understood by those in the art to have functionally predictable effects when substituted. Thus the present invention also encompasses equivalent nucleic acids which encode for such equivalent proteins and the embodiments thereof as described for SEQ ID NO.: 1.

The invention also provides for methods of generating hDCS1 protein, by using recombinant DNA technology and the appropriate nucleic acid encoding for hDCS1 protein, fusion protein, or fragments thereof. The invention provides for incorporating an appropriate nucleic acid sequence into a suitable expression vector, the incorporation of any suitable control elements such as promoter, enhancer, either inducible or constitutively expressed. The invention provides for the use of expression vectors with or without at least one additional selectable marker or expressible protein. The invention provides for methods wherein a suitably constructed expression vector is transformed or otherwise introduced into a suitable host cell, and protein is expressed by such a host cell. Thus the present invention also provides for the transformed host cells, which are capable of producing hCDS1 protein, fusion protein, or fragments thereof.

The discovery that hCDS1 acts in coordination with Cdc25 in the DNA damage checkpoint allows for the use of the compounds of the invention in methods for therapeutic treatment of diseases which involve abnormal DNA damage checkpoint function. The present invention further provides for the use of the compounds of the present invention as therapeutics for the treatment of cancer. In particular, the present invention allows for the specific modification of the hDCS1-Cdc25 DNA damage checkpoint in cells.

The present invention also encompasses methods for screening test compounds for efficacy in effecting the hDCS1 mediated checkpoint function of eukaryotic cells, said method comprising contacting a test compound to eukaryotic cells, and detecting any change in hDCS1 expression or function. Thus the invention further encompasses the method of screening wherein said detection of change in hDCS1 expression or function is accomplished by assaying for hDCS1 mRNA production, or by assaying for hDCS1 protein expression. In particular, the present invention allows for the screening of candidate substances for efficacy in modifying the DNA damage checkpoint by screening for any change in Cdc25 phosphorylation, or kinase activity. The compounds or substances identified by the assays of the invention, or compounds corresponding to such compounds or substances, can be used for the manufacture of pharmaceutical therapeutics.

Thus, in one embodiment the present invention provides for pharmaceutical compositions which include the hCDS1 protein, hCDS1 nucleic acid, hCDS1 anti-sense nucleic acids. In another embodiment, the present invention provides for compounds or substances identified as suitable for use as a therapeutic by the assays of the invention, in pharmaceutical formulations. These pharmaceutical compositions can further include chemotherapeutic agents for the use in treating cancer, or be administered in a regimen coordinated with the administration of other anti-cancer therapies. The present invention, in one embodiment thus encompasses methods for combined chemotherapy using the hCDS1 derived pharmaceuticals independently, and in combination with other chemotherapeutic agents, and in a second embodiment as admixtures with other anti-cancer therapeutics for single dose administration.

According to one aspect of the present invention, there is provided a nucleic acid encoding hDCS1 protein having the amino acid sequence illustrated in FIG. 2 (SEQ ID NO.: 2), or encoding a functional equivalent fragment, or bioprecursor of said protein. Preferably, the nucleic acid may be a DNA molecule such as a genomic DNA molecule and even more preferably a cDNA molecule, however it may also be RNA.

In a preferred embodiment, a nucleic acid encoding hDCS1 protein comprises the nucleic acid sequence represented by position 66 to 1694 of the sequence illustrated in FIG. 1 (SEQ ID NO.: 1), the complement thereof, or a nucleic acid sequence capable of hybridizing to either under high stringency conditions.

The nucleic acid sequences defined herein may, advantageously, be capable of hybridizing under low stringency conditions to nucleic acid sequences derived from family members to identify homologs therefrom or alternatively to identify nucleic acid sequences from other species.

As would be well known to those skilled in the art due to the degeneracy of the genetic code the nucleic acid sequences according to the invention may include substitutions therein yet which still encode the same amino acid sequence.

Advantageously, the nucleic acids according to the invention may be incorporated into an expression vector and may be subsequently used to transform, transfect or infect a suitable host cell. In such an expression vector the nucleic acid according to the invention is operably linked to a control sequence, such as a suitable promoter or the like, ensuring expression of the proteins according to the invention in a suitable host cell. The expression vector may, advantageously be a plasmid, cosmid, virus or other suitable vector. The expression vector and the host cell transfected, transformed or infected with the vector also form part of the present invention. Preferably, the host cell is a eukaryotic cell or a bacterial cell and even more preferably a mammalian cell or insect cell. Mammalian host cells are particularly advantageous because they provide the necessary post-translational modifications to the expressed proteins according to the invention, such as glycosylation or the like, which modifications confer optimal biological activity on said proteins, which when isolated may advantageously be used in diagnostic kits or the like.

The expression vector including said nucleic acid according to the invention may advantageously be used in vivo, such as in, for example, gene therapy.

According to a further aspect of the invention there is also provided a transgenic cell, tissue or organism comprising a transgene capable of expressing hDCS1 protein, which protein comprises the amino acid sequence illustrated in FIG. 2 (SEQ ID NO.: 2), or the amino acid sequence of a functional equivalent or bioprecursor or fragment therefor. The term "transgene capable of expression" as used herein means a suitable nucleic acid sequence which leads to expression of hDCS1 or proteins, having the same function and/or activity. The transgene may include. for example, genomic nucleic acid isolated from human cells or synthetic nucleic acid, including DNA integrated into the genome or in an extrachromosomal state. Preferably, the transgene comprises the nucleic acid sequence encoding the proteins according to the invention as described herein, or a functional fragment of said nucleic acid. A functional fragment of said nucleic acid should be taken to mean a fragment of the gene comprising said nucleic acid coding for the proteins according to the invention or a functional equivalent, derivative or a non-functional derivative such as a dominant negative mutant, or bioprecursor of said proteins. For example, it would be readily apparent to persons skilled in the art that nucleotide substitutions or deletions may be used using routine techniques. which do not affect the protein sequence encoded by said nucleic acid, or which encode a functional protein according to the invention.

The hDCS1 protein expressed by said transgenic cell, tissue or organism or a functional equivalent or bioprecursor of said protein also forms part of the present invention.

Further provided by the present invention is an antisense molecule which is capable of hybridizing to the nucleic acid according to the invention. Advantageously, the antisense molecule according to the invention may be used as a medicament, or in the preparation of a medicament for the treatment of cancer and other proliferative diseases.

The present invention also advantageously provides nucleic acid sequences of at least approximately 15 nucleotides of a nucleic acid according to the invention and preferably from 15 to 50 nucleotides. These sequences may advantageously be used as probes or primers to initiate replication, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridizing conditions and detecting for the presence of any duplex or triplex formation between the probe and any nucleic acid in the sample.

Advantageously, the nucleic acid sequences, according to the invention may be produced using such recombinant or synthetic means, such as for example using PCR cloning mechanisms which generally involve making a pair of primers, which may be from approximately 15 to 50 nucleotides spanning a region of the gene which is desired to be cloned, bringing the primers into contact with mRNA, cDNA, or genomic DNA from a human cell, performing a polymerase chain reaction under conditions which bring about amplification of the desired region (and where necessary first performing a reverse transcription step), isolating the amplified region or fragment and recovering the amplified DNA. Generally, such techniques as defined herein are well known in the art, such as described in Sambrook et. al., (*Molecular Cloning; a Laboratory Manual*, 1989). Advantageously, human allelic variants of the nucleic acid according to the invention may be obtained by for example, probing genomic DNA libraries from a range of individuals for example from different populations, and other genotyping techniques. Furthermore, nucleic acids and probes according to the invention may be used to sequence genomic DNA from patients, using techniques well known in the art, for example, the Sanger dideoxy chain termination method, which may advantageously ascertain any predisposition of a patient to certain proliferative disorders.

Further provided by the present invention are isolated proteins having the amino acid sequences as illustrated in FIG. 2 (SEQ ID NO.: 2) or the amino acid sequence of a functional equivalent functional fragment or bioprecursor of said protein in addition to antibodies, monoclonal or polyclonal capable of binding to the amino acid sequences of these proteins or fragments thereof. As would be well known to those skilled in the art, the proteins according to the invention may comprise conservative substitutions, deletions or insertions wherein the protein comprises different amino acids than those disclosed in FIG. 2, yet which substitutions, deletions or insertions do not affect the activity of the proteins according to the invention or their ability to interact in the human cell cycle checkpoint pathway.

Preferred fragments include those comprising an epitope of the proteins according to the invention. The epitopes may be determined using, for example, peptide scanning techniques as described in Geysen et. al., *Mol. Immunol.*, 23; 709–715 (1986).

The antibodies according to the invention may be produced according to techniques which are known to those skilled in the art. Monoclonal antibodies may be prepared using conventional hybridoma technology as described in Kohler F and Milstein C (1985), *Nature* 256, 495–497. Polyclonal antibodies may also be prepared using conventional technology well known to those skilled in the art, and which comprises inoculating a host animal, such as a mouse, with a protein or epitope according to the invention and recovering the immune serum. The present invention also includes fragments of whole antibodies which maintain their binding activity, such as for example, Fv, F(ab') and F(ab')$_2$ fragments as well as single chain antibodies.

Advantageously, the nucleic acid and/or the proteins according to the invention may be included in a pharmaceutical composition together with a pharmaceutically acceptable carrier, diluent or excipient therefor. The pharmaceutical composition containing said nucleic acids according to the invention may, for example, be used in gene therapy. Such nucleic acids, according to the invention, may be administered naked, or packaged in protein capsules, lipid capsules, liposomes, membrane based capsules, virus protein, whole virus, cell vectors, bacterial cell hosts, altered mammalian cell hosts, or other such suitable means for administration.

There is further provided by the present invention a method for detecting for the presence or absence of a nucleic acid according to the invention, in a biological sample, which method comprises, a) bringing said sample into contact with a probe comprising a nucleic acid or probe according to the invention under hybridizing conditions, and b) detecting for the presence of hybridization, for example, by the presence of any duplex or triplex formation between said probe and any nucleic acid present in said sample. Proteins according to the invention may also be detected by a) contacting said sample with an antibody to an epitope of a protein according to the invention under conditions which allow for the formation of an antibody-antigen complex, b) monitoring for the presence of any antigen-antibody complex.

Kits for detecting said nucleic acids and proteins are also provided by the present invention. A kit for detecting for the presence of a nucleic acid according to the invention in a biological sample may comprise (a) means for contacting the sample with a probe comprising a nucleic acid or a probe according to the invention and means for detecting for the presence of any duplex or triplex formation between said probe and any nucleic acid present in the sample.

Likewise, a kit for detecting for the presence of a protein according to the invention in a biological sample may comprise (a) means for contacting said sample with an antibody to an epitope of a protein according to the invention under conditions which allow for the formation of an antibody—protein complex, and means for monitoring said sample for the presence of any protein—antibody complex.

A further aspect of the present invention provides a method of determining whether a compound is an inhibitor or an activator of expression or activity of the proteins of the human cell cycle checkpoint pathway which method comprises contacting a cell expressing the proteins in said pathway with said compound and comparing the level of expression of any of the proteins of the checkpoint pathway of said cell against a cell which has not been contacted with said compound. Any compounds identified may then advantageously be used as a medicament or in the preparation of a medicament for treating cancer or proliferative disorders. Alternatively, the compounds may be included in a pharmaceutical composition together with a pharmaceutically acceptable carrier, diluent or excipient therefor. Advantageously, any compounds identified as an inhibitor of the cell checkpoint pathway may be included in a pharmaceutical composition according to the invention together with a cytotoxic agent, such as a DNA damaging chemotherapeutic agent, and a pharmaceutically acceptable carrier diluent or excipient therefor. Thus, the human cell cycle checkpoint inhibitor may enhance the chemotherapeutic effect of cytotoxic agents used in, for example, anti-cancer therapy.

There is also provided by the present invention a method for screening candidate substances for anti-cancer therapy, which method comprises a) providing a protein according to the present invention exhibiting kinase activity together with a substrate for said protein under conditions such that the kinase will act upon the substrate, b) bringing the protein and substrate into contact with a candidate substance, c) measuring the degree of any increase or decrease in the kinase activity of the protein, d) selecting a candidate substance which provides a decrease or increase in activity. Such a candidate substance may also be used as a medicament, or in the preparation of a medicament for the treatment of cancer or other such proliferative cell disorders.

The present invention also comprises a method of identifying other proteins active in the cell checkpoint pathway, which method comprises a) contacting a cell extract with an antibody to an epitope of a protein according to the invention, under appropriate binding conditions, b) identifying any antibody-protein complex and c) analyzing the complex to identify any protein bound to the antibody or protein which is other than the protein according to the invention.

Another method for identifying proteins involved in the cell checkpoint pathway utilizes a two-hybrid system developed in yeast by Chien et. al., supra (1991). This technique is based on functional in vivo reconstitution of a transcription factor which activates a reporter gene. More particularly the technique comprises providing an appropriate host cell with a DNA construct comprising a reporter gene under the control of a promoter regulated by a transcription factor having a DNA binding domain and an activating domain, expressing in the host cell a first hybrid DNA sequence encoding a first fusion of a fragment or all of a nucleic acid sequence according to the invention and either said DNA binding domain or the activating domain of the transcription factor, expressing in the host cell at least one second hybrid DNA sequence encoding putative binding proteins to be investigated together with the DNA binding domain or activating domain of the transcription factor which is not incorporated in the first fusion; detecting any binding of the protein being investigated with a protein according to the invention by detecting for the production of any reporter gene product in the host cell; optionally isolating second hybrid DNA sequences encoding the binding protein. In one embodiment of this aspect of the invention the method may comprise:

(a) constructing at least two nucleotide vectors, the first of which comprises a nucleotide segment encoding for a DNA binding domain of GAL4 protein operably linked to a nucleic acid sequence encoding a protein according to the present invention, the second vector comprising a nucleotide sequence encoding a protein binding domain of GAL4 operably linked to a nucleotide sequence encoding a protein to be tested, (b) co-transforming each of said vectors into a yeast cell being deficient for transcription of genes encoding galactose metabolizing proteins, wherein interaction between said test protein and the protein according to the invention leads to transcription of galactose metabolic genes.

BRIEF DESCRIPTION OF THE DRAWINGS

The invention may be more clearly understood from the following examples which are given by way of example only, with reference to the accompanying drawings, wherein:

FIG. 1 illustrates the nucleotide sequence of hCDS1 cDNA (SEQ ID NO.: 1) wherein residues 66–1694 is the coding region, and depect the 3' and 5' untranslated regions (UTRs). The initiation and termination codons are shown in bold, FIG. 2 illustrates the deduced amino acid sequence of hCDS1 (SEQ ID NO.: 2), FIG. 3 illustrates the amino acid sequence alignment of hDCS1 and *S. pombe* cds1 performed using the CLUSTALW alignment program and annotated using the GENEDOC program. Residues shaded black are identical between the two proteins and residues shaded grey are similar.

DETAILED DESCRIPTION OF THE PREFERRED EMBODIMENTS

The present invention encompasses the isolation and characterization of a novel human checkpoint kinase gene and protein which is called hCDS1. The hCDS1 gene and protein show some similarity to a homologous gene and protein found in *S. pombe*.

The *S. pombe* cds1+gene was identified by its ability to complement a DNA polymerase a mutant (Murakami & Okayama, 1995, *Nature*, 374: 817–819). *S. pombe* cds1 was also able to suppress the hydroxyurea sensitivity (DNA replication-dependent checkpoint) of rad1, rad3 and rad9 mutant *S. pombe* strains but not the UV sensitivity (DNA damage-dependent checkpoint). This shows that *S. pombe* cds1 executes its checkpoint function during DNA synthesis.

*S. pombe* cds1 is a putative protein kinase that is 70% similar to the *S. cerevisiae* checkpoint gene RAD53. In *S. cerevisiae* the DNA damage- and DNA replication-dependent checkpoints are genetically separate at the level of detection of DNA lesions. The two pathways then converge on the Rad53 protein kinase which potentially acts as an amplifier in the signal transduction pathway. This appears not to be the case in *S. pombe* where the same proteins are involved in detection of all types of lesion but the transduction of the signal follows separate pathways involving different protein kinases; *S. pombe* cds1 for the DNA replication-dependent checkpoint and Chk1/Rad27 for the DNA damage-dependent pathway. It has been suggested that S-phase-specific activation of cds1 kinase may define a subpathway of the checkpoint response in *S. pombe* (Lindsay et al., 1998, *Genes and Development*, 12: 382–395).

*S. pombe* cds1 may act via an interaction with DNA polymerase α to monitor the progress of DNA replication or the integrity of replication complexes. There is evidence in Drosophila for a kinase of the appropriate molecular weight associating with DNA polymerase α (Peck et al., 1993, *B.B.R.C.*, 190: 325.331). Alternatively it may act via phosphorylation of p107$^{wheel}$ we in a manner analogous to Chk1 ultimately affecting the activity of the G1/S phase cyclin dependent kinases.

Many of the methods and materials for carrying out the basic molecular biology manipulations as described in the examples below are known in the art, and can be found in such references as Sambrook et al., *Molecular Cloning*, 2nd edition, Cold Spring Harbor Laboratory Press (1989); Berger et al., *Guide to Molecular Cloning Techniques, Methods in Enzymology*, Vol. 152, Academic Press, Inc., (1987); Davis et al., *Basic Methods in Molecular Biology*, Elsevier Science Publishing Co., Inc. (1986); Ausubel et al., *Short Protocols in Molecular Biology*, 2nd ed., John Wiley & Sons, (1992); Goeddel *Gene Expression Technology, Methods in Enzymology*, Vol. 185, Academic Press, Inc., (1991); Guthrie et al., *Guide to Yeast Genetics and Molecular Biology, Methods in Enzymology*, Vol. 194, Academic Press, Inc., (1991); McPherson et al., *PCR Volume* 1, Oxford University Press, (1991).

The invention in its several aspects can be more readily understood by reviewing the following examples.

EXAMPLE 1

Isolation of hCDS1

Isolation of hCDS1 began with a search for sequences similar to *S. pombe* cds1+ using the TBLASTN program. A human expressed sequence tag (EST No. 864164) was identified in the proprietary LifeSeq® database (Incyte Pharmaceuticals Inc., Palo Alto, Calif., USA). Sequence analysis of the 1.3 kb insert revealed an incomplete open reading frame which was similar to *S. pombe* cds1. Approximately 650 nucleotides of novel 5' DNA sequence was obtained by 5'RACE (rapid amplification of cDNA ends) using a Marathon Ready human placental cDNA (Clontech), following the manufacturer's instructions.

Briefly, the two hCDS1 gene specific primers used for nested PCR (Polymerase chain reaction) reactions were GSP3 5'-TTTTGCTGATGATCTTTATGGCTAC-3' (SEQ ID NO.: 3) and GSP4 5'-CACAGGCACCACTTCCAAGAGTTTT-3' (SEQ ID NO.: 4). Subsequently, a complete ORF for hDCS1 was amplified from a human SK-N-MC neuroblastoma cDNA library using the PCR primers 5'-GGGCTCGA-GAGCAGCGATGTCTCGGGAGTCGGATGT-3' (SEQ ID NO.: 5) and 5'-GGCGGATCCTCGAGTCACAACACAG-CAGCACACAC-3' (SEQ ID NO.: 6). The amplification product was then cloned into pCR2.1 vector (Invitrogen) and the DNA sequence determined.

The nucleic acid sequence of hCDS1 was found to show 47.8% identity to the *S. pombe* cds1+ at the DNA level. Termination codons were present in all three reading frames in the 120 nucleotides immediately 5' to the putative hDCS1 initiation codon, indicating that the complete coding region has been isolated. Parts of the sequence were also found to match partial sequences found in the NCBI databases, EST AA285249, genomic sequence H55451, and the 54 base pair fragment H55698.

The identified human gene and vectors encoding the hCDS1 nucleic acid sequence were deposited as plasmid HCDS1 ORF/pCR-Blunt deposited under Accession No. LMBP 3708; plasmid HCDS1 5'RACE fragment/pGEM-Easy deposited under Accession No. LMBP 3710; and plasmid HCDS1 3'fragment Incyte clone 864164/pSPORT deposited under Accession No. LMBP 3709 with the Belgian Co-ordinated Collections of Micro-organisms (BCCM) at Laboratorium Voor Moleculaire Biologies-Plasmidencollecte (LMBP) 35, B-9000 Gent, Belgium, in accordance with the provisions of the Budapest Treaty, Apr. 28, 1997.

The tissue expression profile of hDCS1 was examined on multiple tissue Northern blots (Clontech) and a cancer cell line Northern blot (Clontech), which were probed with the hDCS1 ORF. A single transcript of approximately 2.1 kb was observed. Expression was undetectable by conventional Northern blot hybridization conditions in all normal human tissues examined. However, expression was found to be greatly elevated in all of the cancer cell lines examined.

The hDCS1 gene was localized to chromosome 22q11.2-q12, as determined using the complete ORF as a probe for FISH (Fluorescent in situ Hybridization) analysis. The hybridization efficiency was approximately 62%, and no other loci were detected under the conditions used.

Briefly, lymphocytes isolated from human blood were cultured in α-minimal essential media (MEM) supplemented with 10% fetal calf serum and phytohaemagglutinin (PHA) at 37° C. for 68–72 hours. The lymphocyte cultures were treated with BrdU (0.18 mg/ml, Sigma) to synchronize the cell population. The synchronized cells were washed three times with serum-free medium to release the block and re-cultured at 37° C. for 6 hours in α-MEM with thymidine (2.5 μg/ml Sigma). Cells were harvested and slides were prepared using standard procedures including hypotonic treatment, fixation and air-drying. DNA fragments containing the hCDS1 complete ORF were gel purified and biotinylated with dATP using the BRL BioNick labeling kit (15° C., 1 hour) (Heng et al., 1992, *Proc. Natl. Acad. Sci. USA*. 89: 9509–9513).

Slides were then baked at 55° C. for 1 hour, and after RNase treatment, the slides were denatured in 70% formamide in 2×SSC for 2 minutes at 70° C. followed by dehydration with ethanol. Probes were denatured at 75° C. for 5 minutes in a hybridization mix consisting of 50% formamide and 10% dextran sulphate. Probes were loaded on the denatured chromosomal slides. After overnight hybridization, slides were washed and detected. FISH signals and the DAPI-banding pattern were recorded separately by taking photographs, and the assignment of the FISH mapping data with chromosomal bands was achieved by superimposing FISH signals with DAPI banded chromosomes (Heng & Tsui, 1994, *Methods in Mol. Biol.*, 33: 35–49).

EXAMPLE 2

Characterization of hCDS1 Protein

The hDCS1 nucleic acid sequence cDNA predicts a translation product of 543 amino acids with an approximate molecular weight of 61 kDa. This is close to the apparent molecular weight of endogenous Cds1 protein in HeLa cells. The predicted hDCS1 protein, is 28% identical to the cds1 protein of *S. pombe*, 28% identical to RAD53 and 27% identical to the DUNI kinase of *S. cerevisiae*. Sequence alignment of these apparent homologs shows several regions of sequence similarity outside the kinase domain, including conservation of the Fork Head Associated domain (Hoffrnann et al., 1995, *Trends Biochem. Sci.*, 20: 347–9). The human protein shows the same overall structure as *S. pombe* CDS1 and *S. cerevisiae* DUN1 in that it lacks the long C-terminal extension found in RAD53. Northern blot analysis with hCDS1 identified a single transcript of about 2.2 kb expressed in testis and in 8 human cancer samples examined.

Briefly, two multiple tissue Northern blots (Clontech) and a Cancer Cell line Northern blot (Clontech) were hybridized with a cDNA probe for hCDS1. The probe corresponds to the complete ORF as described above. The blots were washed at high stringency (0.1×SSC, 0.1% SDS, 50° C., 2×20 min) and exposed using Kodak X-OMAT autoradiography film with intensifying screens at −70° C.

EXAMPLE 3

Cdc25 Total Activity Assay

The possibility that dephosphorylation of Cdc2 is down-regulated in the presence of DNA damage required an assay to allow for the analysis of the total activity of Cdc25. In the presence of EDTA, Cdc2/Cyclin B from asynchronous HeLa cell extracts was found to inactivate spontaneously.

Briefly, cells were lysed in ice-cold lysis buffer (50 mM Tris pH 7.4 containing 2 mM magnesium chloride, 1 mM phenylmethylsulphonyl fluoride, and 5 μg/ml leupeptin, pepstatin and aprotinin). Lysates were cleared by centrifugation at 10,000×g for 10 minutes and the protein concentration of the supernatants determined using the Lowry assay. 10 mM EDTA was added to the supernatants (100 μg in 60 μL) and the reaction initiated by incubation at 30° C. At assay intervals the activity of Cdc2/Cyclin B was assayed by measuring the histone-H1 kinase activity present in anti-Cyclin B immune-precipitates (Blasina et al., supra.). For immunoblots 400 μg of cell lysate was immune-precipitated using anti-Cyclin B antibody, resolved on an 11% acrylamide-SDS gel. Monoclonal antibody against the PSTAIRE motif of Cdc2 was used to detect the different phospho-forms of Cdc2.

Activation correlates with loss of the inhibited-phosphorylated form of Cdc2, visualized as the slower migrating species on SDS-PAGE gels. Activation was prevented by vanadate, an inhibitor of Cdc25 and other tyrosine phosphatase. Furthermore, immune-depletion with Cdc25C-specific anti-sera greatly reduced activation of Cdc2/Cyclin B. There was no increase in the levels of Cdc2 or Cyclin B protein, phosphorylation by WEE1 and Myt1 was blocked by the presence of 10 mM EDTA. Thus, these result demonstrate that the activation of Cdc2 was the result of dephosphorylation. In lysates of asynchronous HeLa cells, the endogenous Cdc25 phosphatase activity is sufficient to dephosphorylate and activate more than 80% of the available Cyclin B/Cdc2 in 30 minutes. Analysis of lysates of HeLa cells in which the DNA had been damaged by exposure to 10 Gy of τ-irradiation one hour before harvesting showed a significant reduction in the rate of activation of Cdc2, such that less than 25% of the available Cdc2/Cyclin B was activated during the 30 minutes incubation. The amount of Cdc2/Cyclin B in complex was not significantly altered and it was activated to the same extent as control Cdc2/Cyclin B by addition of exogenous GST-Cdc25. Irradiation with 10 Gy led to more than 3-fold reduction in the rate of Cdc2 dephosphorylation in the 10 time courses examined. If the inactivation of Cdc25 measured above is part of the DNA-damage checkpoint response in human cells, then experimental conditions that over-ride the DNA damage checkpoint might be expected to block the radiation-induced inhibition of Cdc25.

EXAMPLE 4

DNA Damage Checkpoint Effect of hCDS1

DNA damage response in a variety of cells is known to require various related kinases which structurally are related to PI-3 kinases. At least one member of the family, DNA-Protein Kinase, has been shown to be sensitive to wortmannin in vitro (Hawley et al., 1996, *Genes and Dev.*, 10: 2383–8; Hartley et al., 1995, *Cell*, 82: 849–856). Thus the possibility that a wortmannin-sensitive kinase acted upstream of the radiation induced delay in M-phase entry was tested (Price et al., 1996, *Cancer Research*, 56: 246–250). HeLa cells can be arrested in M-phase by nocodazole, irradiation causes cells to delay in G2 prior to the nocodazole-sensitive M-phase block point. Thus, by scoring the mitotic index of cells that are cultured in nocodazole, it is possible to determine whether entry into mitosis has been delayed. Control cells cultured in the presence of nocodazole for 14 hours contained 60% mitotic cells, the presence of wortmannin had little effect on this number. However, irradiation reduced the number of cells that reach the nocodazole block point to only 10%. In contrast, irradiation in the presence of wortmannin had only a modest effect. These results demonstrate that wortmannin over-rides the DNA damage G2 checkpoint in HeLa cells.

The effects of wortmannin on the radiation-induced inactivation of Cdc25 was then tested. Wortmannin had little effect on the activation of Cdc2/Cyclin B in extracts prepared from unirradiated cultures, however it did greatly diminish the irradiation-induced decrease in Cdc25 activity.

Radiation-induced G2 checkpoint is also over-ridden in cell-lines derived from patients with the genetic disorder ataxia telangiectasia. Ataxia Telangiectasia mutant cells are defective in both the G1 and G2 checkpoints following exposure to many, but not all, agents that damage DNA (Camnan et al., 1994, *Cancer Research*, 54: 5054–5058). The failure of AT-deficient cells to delay G1 correlates with a failure to up-regulate p53 (Kastan et al., 1992, *Cell*, 71: 587–589), and with failure to phosphorylate and activate cAb1 (Baskaran et al;, 1997, *Nature*, 387: 516–519; Shafman et al., 1997, *Nature*, 387: 520–523). The molecular basis for the failure to delay G2 is unknown. AT-deficient cells show greatly reduced responses to agents that generate chromosomal breaks, such as ionizing τ-rays. Remarkably, AT-deficient cells have near normal responses following the base damage that is generated by irradiation with a UV source (Canman et al., 1994, *Cancer Research*, 54: 5054–5058; Painter et al., 1980, *Proc. Natl. Acad. Sci. USA*, 77: 7315–7317; Zampetti-Bosseler et al., 1981, *Int. J. Radiat. Biol.*, 39: 547–558). The effects of UV and τ-irradiation on the Cdc25 activity of AT-plus and AT-minus SV40-transformed human fibroblast cell-lines was tested. AT-minus cells respond to UV-irradiation with a robust reduction in the rate at which Cdc2 is dephosphorylated. In contrast, τ-irradiation had only a modest effect on the rate of dephosphorylation of Cdc2. In AT-plus cells the rate of dephosphorylation of Cdc2 was significantly reduced following either ionizing-radiation or WV-radiation. These data indicate that the ATM gene product is required for the efficient inactivation of Cdc25 following τ-irradiation and demonstrate a correlation between inactivation of Cdc25 and delayed entry into M-phase following DNA damage.

Mediators of the checkpoint-dependent inactivation of Cdc25 in human cells are excellent targets for generating therapeutics or therapeutic regimens that will enhance anti-cancer treatment, and reduce side-effects on normal cells.

To facilitate biochemical characterization of hCDS1, 6his-hCDS1 was expressed in insect cells, affinity purified and incubated in extracts of HeLa cells in the presence of an ATP-regenerating system. EDTA was added to inhibit kinase in the extract, and the rate of dephosphorylation and activation of Cdc2/CyclinB was monitored.

Briefly, recombinant viruses encoding for 6his-hCDS1, 6his-Chk1, 6his-Cdc2 and GST-Cdc25C were generated using the Bac-to-Bac expression system from Gibco/BRL. 6his-fusion proteins were purified following the procedure described in Kumagai et al., (1995), *Mol. Biol. Cell*, 6: 199–213. GSH-sepharose beads were incubated for 15 minutes in Sf9 extracts; beads were collected by centrifugation and washed three-times with lysis buffer (50 mM Tris pH 8.0, 5 mM EDTA, 150 mM NaCl, 0.1% NP40, 5% glycerol, 0.1% β-mercaptoethanol and protease inhibitors). Beads were washed three-times with kinase assay buffer (50 mM Tris pH 7.4, 10 mM $MgCl_2$) prior to phosphorylation reactions or three-times with phosphatase assay buffer (50 mM imidazole pH 7.4, 5 mM EDTA and 0.1% β-mercaptoethanol) prior to phosphatase assays.

Both 6his-Chk1 and 6his-hCDS1 were found to significantly reduce the activation of Cdc2/Cyclin B in these assays. The reduced activation of Cdc2 was dose dependent and required ATP. Confirmation that Cdc2 was not irreversibly inhibited by 6his-Chk1 or 6his-hCDS1 was shown by the activation that resulted when excess GST-Cdc25C was added after kinase treatment. Thus, both 6his-hCDS1 and 6his-Chk1 can mimic the radiation-induced down-regulation of Cdc25 seen in extracts. These experiments used HeLa cell lysates that had been clarified by centrifugation, therefore it is unlikely that changes in sub-cellular locale could account for inactivation of Cdc25 (Peng et al., 1997, *Science*, 277: 1501–1505).

EXAMPLE 5

Direct Effect of hCDS1 on Cdc25

Indirect mechanisms of inhibition of Cdc25 by hCDS1 could not be excluded by the cell lysate assays, therefore, affinity-purified reagents were used to determine direct phosphorylation and inhibition of GST-Cdc25 activity by hCDS1.

GST-Cdc25 was incubated with either 6his-hCDS1, mock beads, or 6his-Chk1 in the presence of $\tau$-$^{32}$P ATP for 15 minutes at 30° C. Proteins were resolved by SDS-PAGE and visualized by autoradiography. GST-Cdc25 was phosphorylated by 6his-Chk1 and by 6his-hCDS1. Assays were performed to determine if Cdc25 phosphatase activity was effected by this phosphorylation.

GST-Cdc25 was assayed for its ability to activate the histone-H1 kinase activity of Cdc2/Cyclin B immune-precipitates. It was found that phosphorylation of GST-Cdc25 by 6his-hDCS1 inhibited the ability of GST-Cdc25 to activate Cdc2/Cyclin B. Thus, these data demonstrate that 6his-hDCS1 inactivated Cdc25 in vitro, and that Cdc25 is inactivated in vivo following DNA damage.

Since 6his-Chk1 associates with GST-Cdc25 and has histone-H1 kinase activity in vitro (Sanchez et al., 1997, *Science*, 277: 1497–1501), analysis of Cdc2/Cyclin B kinase activity was obscured. In order to test GST-Chk1 effects, an assay was used in which Cdc2 dephosphorylation was monitored by the disappearance of the slower migrating species of Cdc2 on gel-mobility analysis.

Briefly, phosphorylated Cdc2 was purified from Sf9 cells that had been simultaneously infected with recombinant baculoviruses encoding 6his-Cdc2, 6his-Wee1, 6his-Myt1 and GST-Cyclin B (Parker et al., 1992, *Science*, 257: 1955–1957. The 6his-Cdc2 complexed to Cyclin B was purified using GSH beads under the conditions for GST-Cdc25 except that 1 mM $VO_4$ was included in the lysis buffer. Western Blot analysis showed that quadruple infection resulted in phosphorylation of the majority of Cdc2/GST-Cyclin B at one or both inhibitory sites. These phosphatase assays were carried out in the presence of 10 mM EDTA, and the absence of ATP, conditions that eliminate the possibility of 6his-Chk1 phosphorylating Cdc2 or Cyclin B directly. GST-Cdc25 catalyses a reduction in the slower migrating phosphorylated forms of Cdc2. Prior phosphorylation of GST-Cdc25 by 6his-Chk1 leads to a dose-dependent reduction in GST-Cdc25 activity. These data confirm that Chk1 negatively regulated Cdc25 activity (Fumari et al., 1997, *Science*, 277: 1495–1497; Weinert, 1997, *Science*, 277: 1450), and extend them by demonstrating that the negative regulation involves inactivation of the phosphatase activity.

EXAMPLE 6

DNA Damage and Modification of hCDS1

As the previous data had shown that 6his-hCDS1 inactivates Cdc25, and that DNA damage is associated with Cdc25 inactivation, an assay was performed to determine if DNA damage leads to any modification or activation of hCDS1. Antisera raised against 6his-hDCS1 was used in immune-complex kinase assays using HeLa cell lysates. A weak signal corresponding to hCDS1 was detected in the sample from asynchronous HeLa cells; increased phosphorylation of hCDS1 was seen following irradiation.

Briefly, antibodies to hCDS1 were generated by immunizing a rabbit with 6his-hCDS1 purified from Sf9 cells (Harlow et al., *Antibodies* (Cold Spring Harbor Laboratory Press, N.Y., 1988). The resulting antisera immune-precipitates an active kinase of the expected molecular weight from Sf9 cells infected with 6his-hCDS1 virus, but not from uninfected Sf9 cells, or from other cells infected with 6his-Chk1 virus.

The results were confirmed as being due to hCDS1 by re-precipitation of the protein band following denaturation in 4% SDS. The in vitro phosphorylation is most likely due to autophosphorylation, and the increased signal reflects an increase in activity following irradiation. The increase of in vitro phosphorylation of $p64^{Cds1}$ suggests that, like RAD53 and DUN1, hCDS1 is modified in response to DNA damage.

The effect of arresting DNA synthesis on phosphorylation of $p64^{cds1}$ was examined by further assay. The hCDS1 from replication arrested cells behaved exactly like the protein from asynchronous cultures; no significant increase in phosphorylation was seen in response to thymidine or other agents that block DNA replication. The increased phosphorylation of $p64^{cds1}$ was detected following irradiation of thymidine-arrested cells. The effect of damaging DNA in cells that are predominantly arrested outside S-phase was also tested. Cells were cultured in the presence of nocodazole for 20 hours prior to irradiation. Again, a weak but detectable signal was seen in the unirradiated sample. However, irradiation of nocodazole arrested cells led to increased phosphorylation.

These findings surprisingly contrast with the results found in yeast, where fission yeast Cds1 has been found to be activated in response to incompletely replicated DNA (Boddy et al., 1998, *Science*, 280: 909–12; Lindsay et al., 1998, *Genes and Dev.*, 12: 382–95). The results here show a role for human Cds1 in the DNA damage checkpoint rather than the replication checkpoint as previously found in yeast.

EXAMPLE 7

Drug Identification

The Cdc25 assays described above are suitable for use in the identification of chemical agents that would modify the DNA damage checkpoint mediated by hCDS1 and Cdc25, either by enhanced or inhibited activity. Thus a typical screening assay would use similar conditions as described above, plus addition of a reagent to be tested. Monitoring of the activity of the assay components, i.e. detection of phosphorylation as described above, can be conducted in comparison to control reactions to detect both enhanced and inhibited activity.

Clearly such assays are readily adaptable to mechanical/automated apparatus and detection. With the fundamental elements of the assay reactions being known, the assay is clearly suited for use in conjunction with automated high-throughput low-signal apparatus which may incorporate microscopic slide arrays, or cell-biochip arrays in conjunction with CCD detection devices and the use of a visible signal triggered by phosphorylation or other reaction to kinase activity.

EXAMPLE 8

Therapeutic Use

The characterization of hDCS1 and the elucidation that the role for human Cds1 is in the DNA damage checkpoint rather than the replication checkpoint as found in yeast, allows for the adaptation of this knowledge to the preparation of pharmaceuticals, and therapeutic methods for acting as an adjunct to chemotherapy of cancer.

In particular, pharmaceutical formulations of the present invention incorporating cDNA, RNA, antisense molecules, hDCS1 protein, antibodies against hCDS1 protein, or other therapeutics corresponding to those identified in the assays of the invention, can be administered in conjunction with any suitable chemotherapy agent in order to act as an adjunct to the main action of the chemotherapy agent. For example, the use of anticancer drugs such as antimetabolite, antibiotics, alkylating agents, microtubule inhibitors, steroid hormones and their antagonists, and others, is generally directed against metabolic sites essential to cell replication. While ideally these drugs should intervene only with the cellular processes unique to malignant cells, the currently available anticancer drugs affect all proliferating cells, both normal and malignant. Thus, current chemotherapy is hampered by a steep dose-response curve for both toxic and therapeutic effects. Therefore, co-administration of the hCDS1-based drugs of the present invention, and drugs identified by the hCDS1 assays of the present invention, with chemotherapeutic agents will allow for enhanced killing of malignant cells.

One mechanism for enhanced killing is effected by disabling the DNA damage checkpoint control of malignant cells, thus making the administration of DNA damaging chemotherapeutic agents more effective. The disabling of the DNA damage control checkpoint can be effected by modifying the hCDS1 response, as demonstrated by the data above.

Thus, the co-administration of novel hDCS1 based therapeutics in combination with any one or more anticancer agent is contemplated by the present invention. For example. normal dosages of the anticancer drugs Cytarabine, Fludarabine, 5-Fluorouracil, 6-Mercaptopurine, Methotrexate, 6-Thioguanine, Bleomycin, Dactinomycin, Daunorubicin, Doxorubicin, Idarubicin, Plicamycin, Carmustine, lomustine, Cyclophosphamide, Ifosfamide, Mechloroethamine, Streptozotocin, Navelbine, Paclitaxel, Vinblastine, Vincristine, Asparaginase, Cisplatin, Carboplatin, Etoposide, Interferons, Procarbazine etc., can be administered with the appropriate amount of hCDS1 based drug so as to a) alter the length of time of administration, b) alter the time between administrations, c) alter the efficacy of the chemotherapeutic agent on malignant cells, or d) alter the side-effects of the chemotherapeutic agent on normal cells. The effects of the co-administration of hDCS1 based drugs can be any one or combination of these effects in addition to others.

Typically, destruction of cancer cells by chemotherapeutic agents follows first-order kinetics, for a log kill effect. Thus, the co-administration of hCDS1-based therapeutics would be designed to enhance the log kill effect. Typically, chemotherapeutic treatment protocols call for a combination of drugs which act at different steps in the metabolic pathway, thus enhancing killing while staying below toxic levels. Thus, the co-administration of hDCS1 based therapeutics would ideally be in combination with such protocols, and improve efficacy thereof.

Ultimately, the most effective therapeutic methods would combine targeted administration of chemotherapeutic drugs and/or MDR (multidrug resistance) inhibiting agents, with hCDS1 based therapeutics, to specifically target and eliminate malignant cells via the cells' own uncontrolled replication without DNA damage repair, and thus eventual cell death.

The foregoing discussion and examples are intended as illustrative of the present invention and are not to be taken as limiting. Still other variants within the spirit and scope of this invention are possible and will readily present themselves to those of skill in the art.

What is claimed is:

1. An isolated protein having SEQ ID NO.: 2.

\* \* \* \* \*

UNITED STATES PATENT AND TRADEMARK OFFICE
CERTIFICATE OF CORRECTION

PATENT NO. : 6,413,755 B1
DATED : July 2, 2002
INVENTOR(S) : Walter H.M.L. Luyten et al.

It is certified that error appears in the above-identified patent and that said Letters Patent is hereby corrected as shown below:

Column 1,
Line 62, "cds1$_+$" should be -- cds1$^+$ --.

Column 2,
Line 61, "intemucleotide" should be -- internucleotide --.

Column 3,
Lines 12, 15, 18, 29, 50 and 51, "hDCS1" should be -- hCDS1 --.
Line 54, after "vector," insert -- together with --.
Line 55, after "as" insert -- a --; same line, after "promoter," insert -- and/or --.

Column 4,
Lines 6, 9, 11, 14, 15 (2 occurrences), 41 and 49, "hDCS1" should be -- hCDS1 --.

Column 5,
Lines 23, 29 and 48, "hDCS1" should be -- hCDS1 --.

Column 8,
Line 63, "depect" should be -- depicts --.

Column 9,
Line 43, "p107$^{wheel}$" should be -- p107$^{weel}$ --.

Column 10,
Lines 15, 26, 45, 48 and 53, "hDCS1" should be -- hCDS1 --.

Column 11,
Lines 25 and 29, "hDCS1" should be -- hCDS1 --.

Column 13,
Line 28, "WV-radiation" should be -- UV-radiation --.

UNITED STATES PATENT AND TRADEMARK OFFICE
CERTIFICATE OF CORRECTION

PATENT NO. : 6,413,755 B1
DATED : July 2, 2002
INVENTOR(S) : Walter H.M.L. Luyten et al.

It is certified that error appears in the above-identified patent and that said Letters Patent is hereby corrected as shown below:

<u>Column 14,</u>
Lines 24, 26 and 65, "hDCS1" should be -- hCDS1 --.

<u>Column 15,</u>
Line 66, "hDCS1" should be -- hCDS1 --.

<u>Column 16,</u>
Lines 8, 53 and 62, "hDCS1" should be -- hCDS1 --.

Signed and Sealed this

First Day of April, 2003

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 1858
<212> TYPE: DNA
<213> ORGANISM: Homo sapiens
<220> FEATURE:
<221> NAME/KEY: CDS
<222> LOCATION: (66)..(1694)

<400> SEQUENCE: 1

```
actagtgatt actcacaggg ctcgagcggc cgcccgggca ggtcaggtgg gctcacgcgg       60 tcgtg atg tct cgg gag tcg gat gtt gag gct cag cag tct cat ggc agc     110
      Met Ser Arg Glu Ser Asp Val Glu Ala Gln Gln Ser His Gly Ser
      1               5                   10                  15 agt gcc tgt tca cag ccc cat ggc agc gtt acc cag tcc caa ggc tcc       158
Ser Ala Cys Ser Gln Pro His Gly Ser Val Thr Gln Ser Gln Gly Ser
                 20                  25                  30 tcc tca cag tcc cag ggc ata tcc agc tcc tct acc agc acg atg cca       206
Ser Ser Gln Ser Gln Gly Ile Ser Ser Ser Ser Thr Ser Thr Met Pro
            35                  40                  45 aac tcc agc cag tcc tct cac tcc agc tct ggg aca ctg agc tcc tta       254
Asn Ser Ser Gln Ser Ser His Ser Ser Ser Gly Thr Leu Ser Ser Leu
        50                  55                  60 gag aca gtg tcc act cag gaa ctc tat tct att cct gag gac caa gaa       302
Glu Thr Val Ser Thr Gln Glu Leu Tyr Ser Ile Pro Glu Asp Gln Glu
    65                  70                  75 cct gag gac caa gaa cct gag gag cct acc cct gcc ccc tgg gct cga       350
Pro Glu Asp Gln Glu Pro Glu Glu Pro Thr Pro Ala Pro Trp Ala Arg
 80                  85                  90                  95 tta tgg gcc ctt cag gat gga ttt gcc aat ctt gaa tgt gtg aat gac       398
Leu Trp Ala Leu Gln Asp Gly Phe Ala Asn Leu Glu Cys Val Asn Asp
                100                 105                 110 aac tac tgg ttt ggg agg gac aaa agc tgt gaa tat tgc ttt gat gaa       446
Asn Tyr Trp Phe Gly Arg Asp Lys Ser Cys Glu Tyr Cys Phe Asp Glu
            115                 120                 125 cca ctg ctg aaa aga aca gat aaa tac cga aca tac agc aag aaa cac       494
Pro Leu Leu Lys Arg Thr Asp Lys Tyr Arg Thr Tyr Ser Lys Lys His
        130                 135                 140 ttt cgg att ttc agg gaa gtg ggt cct aaa aac tct tac att gca tac       542
Phe Arg Ile Phe Arg Glu Val Gly Pro Lys Asn Ser Tyr Ile Ala Tyr
    145                 150                 155 ata gaa gat cac agt ggc aat gga acc ttt gta aat aca gag ctt gta       590
Ile Glu Asp His Ser Gly Asn Gly Thr Phe Val Asn Thr Glu Leu Val
160                 165                 170                 175 ggg aaa gga aaa cgc cgt cct ttg aat aac aat tct gaa att gca ctg       638
Gly Lys Gly Lys Arg Arg Pro Leu Asn Asn Asn Ser Glu Ile Ala Leu
                180                 185                 190 tca cta agc aga aat aaa gtt ttt gtc ttt ttt gat ctg act gta gat       686
Ser Leu Ser Arg Asn Lys Val Phe Val Phe Phe Asp Leu Thr Val Asp
            195                 200                 205 gat cag tca gtt tat cct aag gca tta aga gat gaa tac atc atg tca       734
Asp Gln Ser Val Tyr Pro Lys Ala Leu Arg Asp Glu Tyr Ile Met Ser
        210                 215                 220
```

```
aaa act ctt gga agt ggt gcc tgt gga gag gta aag ctg gct ttc gag      782
Lys Thr Leu Gly Ser Gly Ala Cys Gly Glu Val Lys Leu Ala Phe Glu
    225                 230                 235 agg aaa aca tgt aag aaa gta gcc ata aag atc atc agc aaa agg aag      830
Arg Lys Thr Cys Lys Lys Val Ala Ile Lys Ile Ile Ser Lys Arg Lys
240                 245                 250                 255 ttt gct att ggt tca gca aga gag gca gac cca gct ctc aat gtt gaa      878
Phe Ala Ile Gly Ser Ala Arg Glu Ala Asp Pro Ala Leu Asn Val Glu
                260                 265                 270 aca gaa ata gaa att ttg aaa aag cta aat cat cct tgc atc atc aag      926
Thr Glu Ile Glu Ile Leu Lys Lys Leu Asn His Pro Cys Ile Ile Lys
            275                 280                 285 att aaa aac ttt ttt gat gca gaa gat tat tat att gtt ttg gaa ttg      974
Ile Lys Asn Phe Phe Asp Ala Glu Asp Tyr Tyr Ile Val Leu Glu Leu
        290                 295                 300 atg gaa ggg gga gag ctg ttt gac aaa gtg gtg ggg aat aaa cgc ctg     1022
Met Glu Gly Gly Glu Leu Phe Asp Lys Val Val Gly Asn Lys Arg Leu
    305                 310                 315 aaa gaa gct acc tgc aag ctc tat ttt tac cag atg ctc ttg gct gtg     1070
Lys Glu Ala Thr Cys Lys Leu Tyr Phe Tyr Gln Met Leu Leu Ala Val
320                 325                 330                 335 cag tac ctt cat gaa aac ggt att ata cac cgt gac tta aag cca gag     1118
Gln Tyr Leu His Glu Asn Gly Ile Ile His Arg Asp Leu Lys Pro Glu
                340                 345                 350 aat gtt tta ctg tca tct caa gaa gag gac tgt ctt ata aag att act     1166
Asn Val Leu Leu Ser Ser Gln Glu Glu Asp Cys Leu Ile Lys Ile Thr
            355                 360                 365 gat ttt ggg cac tcc aag att ttg gga gag acc tct ctc atg aga acc     1214
Asp Phe Gly His Ser Lys Ile Leu Gly Glu Thr Ser Leu Met Arg Thr
        370                 375                 380 tta tgt gga acc ccc acc tac ttg gcg cct gaa gtt ctt gtt tct gtt     1262
Leu Cys Gly Thr Pro Thr Tyr Leu Ala Pro Glu Val Leu Val Ser Val
    385                 390                 395 ggg act gct ggg tat aac cgt gct gtg gac tgc tgg agt tta gga gtt     1310
Gly Thr Ala Gly Tyr Asn Arg Ala Val Asp Cys Trp Ser Leu Gly Val
400                 405                 410                 415 att ctt ttt atc tgc ctt agt ggg tat cca cct ttc tct gag cat agg     1358
Ile Leu Phe Ile Cys Leu Ser Gly Tyr Pro Pro Phe Ser Glu His Arg
                420                 425                 430 act caa gtg tca ctg aag gat cag atc acc agt gga aaa tac aac ttc     1406
Thr Gln Val Ser Leu Lys Asp Gln Ile Thr Ser Gly Lys Tyr Asn Phe
            435                 440                 445 att cct gaa gtc tgg gca gaa gtc tca gag aaa gct ctg gac ctt gtc     1454
Ile Pro Glu Val Trp Ala Glu Val Ser Glu Lys Ala Leu Asp Leu Val
        450                 455                 460 aag aag ttg ttg gta gtg gat cca aag gca cgt ttt acg aca gaa gaa     1502
Lys Lys Leu Leu Val Val Asp Pro Lys Ala Arg Phe Thr Thr Glu Glu
    465                 470                 475 gcc tta aga cac ccg tgg ctt cag gat gaa gac atg aag aga aag ttt     1550
Ala Leu Arg His Pro Trp Leu Gln Asp Glu Asp Met Lys Arg Lys Phe
480                 485                 490                 495 caa gat ctt ctg tct gag gaa aat gaa tcc aca gct cta ccc cag gtt     1598
Gln Asp Leu Leu Ser Glu Glu Asn Glu Ser Thr Ala Leu Pro Gln Val
                500                 505                 510 cta gcc cag cct tct act agt cga aag cgg ccc cgt gaa ggg gaa gcc     1646
Leu Ala Gln Pro Ser Thr Ser Arg Lys Arg Pro Arg Glu Gly Glu Ala
            515                 520                 525 gag ggt gcc gag acc aca aag cgc cca gct gtg tgt gct gct gtg ttg     1694
Glu Gly Ala Glu Thr Thr Lys Arg Pro Ala Val Cys Ala Ala Val Leu
```

```
            530               535             540
tgaactccgt ggtttgaaca cgaaagaaat gtaccttctt tcactctgtc atctttcttt    1754
tctttgagtc tgttttttta tagtttgtat tttaattatg ggaataattg cttttcaca     1814 gtcactgatg tacaattaaa aacctgatgg aacctggaaa aaaa                     1858

<210> SEQ ID NO 2
<211> LENGTH: 543
<212> TYPE: PRT
<213> ORGANISM: Homo sapiens

<400> SEQUENCE: 2

Met Ser Arg Glu Ser Asp Val Glu Ala Gln Gln Ser His Gly Ser Ser
1               5                   10                  15

Ala Cys Ser Gln Pro His Gly Ser Val Thr Gln Ser Gln Gly Ser Ser
            20                  25                  30

Ser Gln Ser Gln Gly Ile Ser Ser Ser Thr Ser Thr Met Pro Asn
        35                  40                  45

Ser Ser Gln Ser Ser His Ser Ser Gly Thr Leu Ser Ser Leu Glu
    50                  55                  60

Thr Val Ser Thr Gln Glu Leu Tyr Ser Ile Pro Glu Asp Gln Glu Pro
65                  70                  75                  80

Glu Asp Gln Glu Pro Glu Pro Thr Pro Ala Pro Trp Ala Arg Leu
                85                  90                  95

Trp Ala Leu Gln Asp Gly Phe Ala Asn Leu Glu Cys Val Asn Asp Asn
            100                 105                 110

Tyr Trp Phe Gly Arg Asp Lys Ser Cys Glu Tyr Cys Phe Asp Glu Pro
        115                 120                 125

Leu Leu Lys Arg Thr Asp Lys Tyr Arg Thr Tyr Ser Lys Lys His Phe
    130                 135                 140

Arg Ile Phe Arg Glu Val Gly Pro Lys Asn Ser Tyr Ile Ala Tyr Ile
145                 150                 155                 160

Glu Asp His Ser Gly Asn Gly Thr Phe Val Asn Thr Glu Leu Val Gly
                165                 170                 175

Lys Gly Lys Arg Arg Pro Leu Asn Asn Asn Ser Glu Ile Ala Leu Ser
            180                 185                 190

Leu Ser Arg Asn Lys Val Phe Val Phe Phe Asp Leu Thr Val Asp Asp
        195                 200                 205

Gln Ser Val Tyr Pro Lys Ala Leu Arg Asp Glu Tyr Ile Met Ser Lys
    210                 215                 220

Thr Leu Gly Ser Gly Ala Cys Gly Glu Val Lys Leu Ala Phe Glu Arg
225                 230                 235                 240

Lys Thr Cys Lys Lys Val Ala Ile Lys Ile Ser Lys Arg Lys Phe
                245                 250                 255

Ala Ile Gly Ser Ala Arg Glu Ala Asp Pro Ala Leu Asn Val Glu Thr
            260                 265                 270

Glu Ile Glu Ile Leu Lys Lys Leu Asn His Pro Cys Ile Ile Lys Ile
        275                 280                 285

Lys Asn Phe Phe Asp Ala Glu Asp Tyr Tyr Ile Val Leu Glu Leu Met
    290                 295                 300

Glu Gly Gly Glu Leu Phe Asp Lys Val Val Gly Asn Lys Arg Leu Lys
305                 310                 315                 320

Glu Ala Thr Cys Lys Leu Tyr Phe Tyr Gln Met Leu Leu Ala Val Gln
                325                 330                 335
```

```
Tyr Leu His Glu Asn Gly Ile Ile His Arg Asp Leu Lys Pro Glu Asn
            340                 345                 350

Val Leu Leu Ser Ser Gln Glu Glu Asp Cys Leu Ile Lys Ile Thr Asp
            355                 360                 365

Phe Gly His Ser Lys Ile Leu Gly Glu Thr Ser Leu Met Arg Thr Leu
        370                 375                 380

Cys Gly Thr Pro Thr Tyr Leu Ala Pro Glu Val Leu Ser Val Gly
385                 390                 395                 400

Thr Ala Gly Tyr Asn Arg Ala Val Asp Cys Trp Ser Leu Gly Val Ile
                405                 410                 415

Leu Phe Ile Cys Leu Ser Gly Tyr Pro Pro Phe Ser Glu His Arg Thr
            420                 425                 430

Gln Val Ser Leu Lys Asp Gln Ile Thr Ser Gly Lys Tyr Asn Phe Ile
            435                 440                 445

Pro Glu Val Trp Ala Glu Val Ser Glu Lys Ala Leu Asp Leu Val Lys
        450                 455                 460

Lys Leu Leu Val Val Asp Pro Lys Ala Arg Phe Thr Thr Glu Glu Ala
465                 470                 475                 480

Leu Arg His Pro Trp Leu Gln Asp Glu Asp Met Lys Arg Lys Phe Gln
                485                 490                 495

Asp Leu Leu Ser Glu Glu Asn Glu Ser Thr Ala Leu Pro Gln Val Leu
            500                 505                 510

Ala Gln Pro Ser Thr Ser Arg Lys Arg Pro Arg Glu Gly Glu Ala Glu
            515                 520                 525

Gly Ala Glu Thr Thr Lys Arg Pro Ala Val Cys Ala Ala Val Leu
        530                 535                 540

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:PCR Primer
      GSP3

<400> SEQUENCE: 3
ttttgctgat gatctttatg gctac                                        25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: PCR Primer
      GSP4

<400> SEQUENCE: 4
cacaggcacc acttccaaga gtttt                                        25

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: PCR Primer

<400> SEQUENCE: 5
gggctcgaga gcagcgatgt ctcgggagtc ggatgt                            36

<210> SEQ ID NO 6
```

-continued

```
<211> LENGTH: 35
<212> TYPE: DNA
<213> ORGANISM: Artificial Sequence
<220> FEATURE:
<223> OTHER INFORMATION: Description of Artificial Sequence: PCR Primer

<400> SEQUENCE: 6
ggcggatcct cgagtcacaa cacagcagca cacac                               35
```